United States Patent
Ha et al.

(10) Patent No.: US 10,265,306 B2
(45) Date of Patent: Apr. 23, 2019

(54) PHARMACEUTICAL COMPOSITION FOR PREVENTING OR TREATING CANCER AND METHOD USING THEREOF

(71) Applicant: MEDPACTO INC., Suwon-si, Gyeonggi-do (KR)

(72) Inventors: Il Ho Ha, Gunpo-si (KR); Seong Jin Kim, Seoul (KR)

(73) Assignee: MEDPACTO INC., Suwon-si, Gyeonggi-Do (KR)

( * ) Notice: Subject to any disclaimer, the term of this patent is extended or adjusted under 35 U.S.C. 154(b) by 0 days.

(21) Appl. No.: 15/549,513

(22) PCT Filed: Apr. 6, 2016

(86) PCT No.: PCT/KR2016/003602
§ 371 (c)(1),
(2) Date: Aug. 8, 2017

(87) PCT Pub. No.: WO2016/163754
PCT Pub. Date: Oct. 13, 2016

(65) Prior Publication Data
US 2018/0021317 A1    Jan. 25, 2018

(30) Foreign Application Priority Data

Apr. 7, 2015 (KR) .................... 10-2015-0049215
Jul. 28, 2015 (KR) .................... 10-2015-0106779

(51) Int. Cl.
| | | |
|---|---|---|
| *A61K 31/444* | (2006.01) | |
| *A61K 39/395* | (2006.01) | |
| *C07K 16/28* | (2006.01) | |
| *A61K 45/06* | (2006.01) | |
| *A61P 35/00* | (2006.01) | |
| *A61K 39/00* | (2006.01) | |

(52) U.S. Cl.
CPC ........ *A61K 31/444* (2013.01); *A61K 39/3955* (2013.01); *A61K 39/39558* (2013.01); *A61K 45/06* (2013.01); *A61P 35/00* (2018.01); *C07K 16/2818* (2013.01); *C07K 16/2827* (2013.01); *A61K 2039/505* (2013.01); *C07K 2317/20* (2013.01); *C07K 2317/76* (2013.01)

(58) Field of Classification Search
CPC ..... A61K 31/444; A61K 39/395; C07K 16/28
See application file for complete search history.

(56) References Cited

U.S. PATENT DOCUMENTS

| 8,513,222 B2 | 8/2013 | Kim et al. |
| 2008/0227824 A1 | 9/2008 | Minidis et al. |
| 2011/0319406 A1 | 12/2011 | Kim et al. |

FOREIGN PATENT DOCUMENTS

JP    2013533252 A    8/2013

OTHER PUBLICATIONS

Tsai et al. Human Vaccines & Immunotherapeutics, Nov. 2014, vol. 10, No. 11, pp. 3111-3116.*
Golub et al., Science, vol. 286, Oct. 15, 1999, pp. 531-537.*
Yamaguchi, "Current situations and the future prospect of monoclonal antibody products", 1, Bull. National Institute of Health Sciences, No. 132, pp. 36-46 (2014).
J. Y. Son, et al; EW-7197, a novel ALK-5 kinase inhibitor, potently inhibits breast to lung metastasis; Molecular Cancer Therapeutics; vol. 13; No. 7; Jul. 2014; pp. 1704-1716.
A. Holtzhausen, et al; Early carcinogenesis involves the establishment of immune privilege via intrinsic and extrinsic regulation . . . ; Frontiers in Immunology; vol. 5; Article 438; Oct. 2014; pp. 1-9.
S. J. Antonia, et al; Immuno-oncology combinations: a review of clinical experience and future prospects; Clinical Cancer Research; vol. 20; No. 24; Dec. 2014; pp. 6258-6268.
International Search Report dated Aug. 26, 2016 for PCT/KR2016/003602.
Written Opinion dated Aug. 26, 2016 for PCT/KR2016/003602.
Activin receptor-like kinaseS inhibition suppresses mouse melanoma by ubiquitin degradation of Smad4, thereby derepressing eomesodermin in cytotoxic T lymphocytes, Jeong-Hwan Yoon et al., EMB0 Mal Med (2013) 5. 1720-173.
First in Human Dose Escalation Study of Vactosertib (TEW-7197) in Subjects With Advanced Stage Solid Tumors, ClinicalTrials.gov Identifier NCT02160106.
EW-7197 inhibits hepatic, renal, and pulmonary fibrosis by blocking TGF-P/Smad and ROS signaling, Sang-A Park et al., Cell. Mol. Life Sci. (2015) 72:2023-2039, DOI 10.1007/s00018-014-1798-6.
Discovery of N-( (4-([ 1,2,4 ]Triazolo[ 1,5-a] pyridi n-6-yl)-5-( 6-methyl pyridi n-2-yl)-1 H-imidazol-2-yl)methyl)-2-fluoroaniline (EW-7197): A Highly Potent, Selective, and Orally Bioavailable Inhibitor of TGF-P Type I Receptor Kinase as Cancer Immunotherapeutic/ Antifibrotic Agent, Cheng Hua Jin et al., J. Med. Chem. 2014, 57, 4213-4238.
The extended European Search Report, Application No. 16776857.1, dated Jun. 12, 2018.

* cited by examiner

*Primary Examiner* — Samira J Jean-Louis
(74) *Attorney, Agent, or Firm* — Lucas & Mercanti, LLP

(57) ABSTRACT

Provided are a pharmaceutical composition for preventing or treating cancer and a method of preventing or treating cancer using the same. Cancer may be effectively prevented or treated using the pharmaceutical composition and method.

8 Claims, 2 Drawing Sheets

[Fig. 1A]
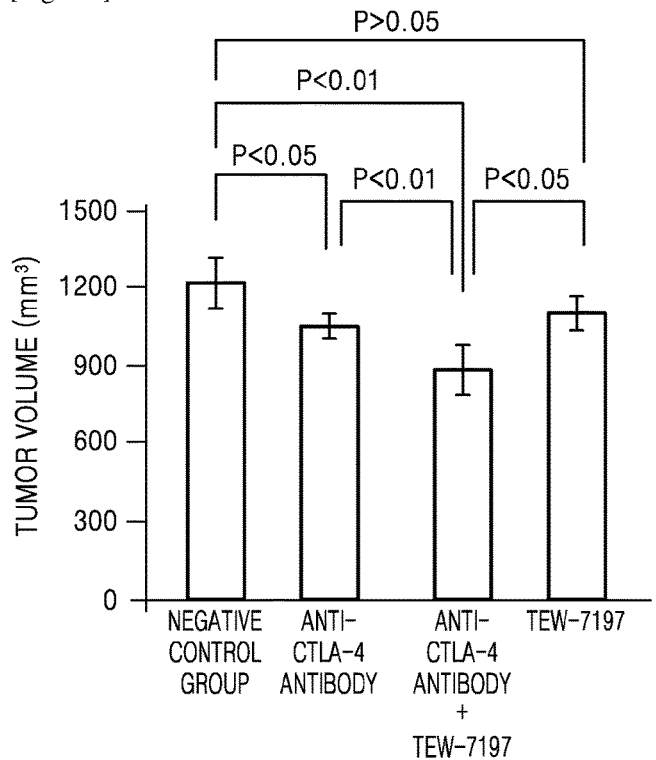
[Fig. 1B]
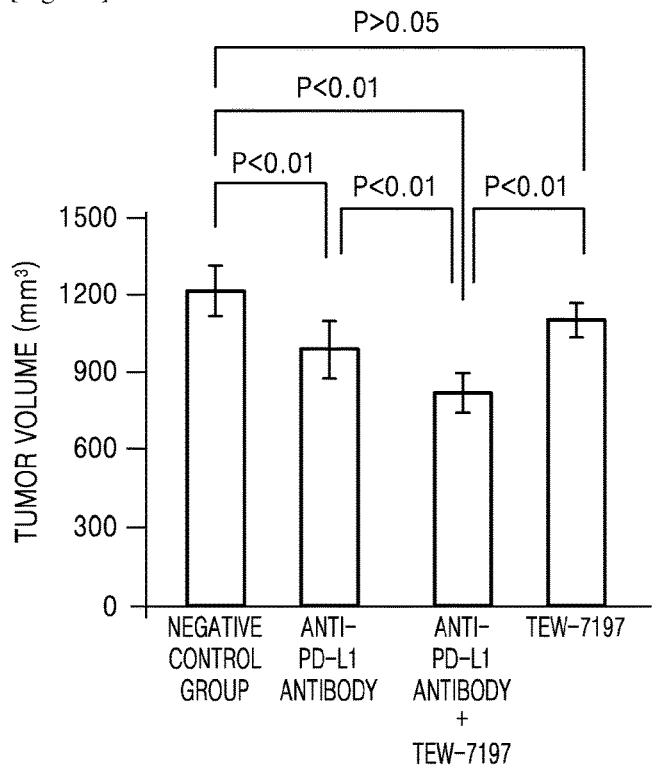

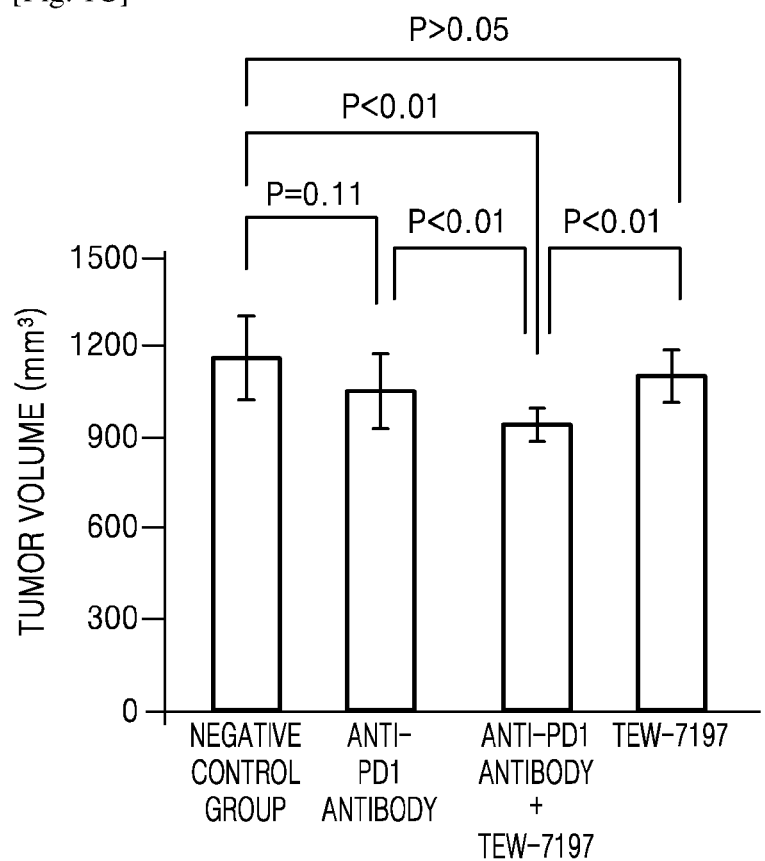
[Fig. 1C]

PHARMACEUTICAL COMPOSITION FOR PREVENTING OR TREATING CANCER AND METHOD USING THEREOF

CROSS-REFERENCE TO RELATED APPLICATIONS

This application is a 371 U.S. National Phase Entry Application of PCT/KR2016/003602, filed Apr. 6, 2016, which claims the priority from Korean Patent Application Nos. 10-2015-0049215, filed Apr. 7, 2015 and 10-2015-0106779 filed Jul. 28, 2915, the contents of each of which are incorporated herein by reference.

TECHNICAL FIELD

The present disclosure relates to a pharmaceutical composition for preventing or treating cancer and a method of treating using the same.

BACKGROUND ART

Cancer immunotherapy refers to a therapy treating cancer using immune system in the body. Cancer cells may have cell surface molecules, e.g., proteins or carbohydrates, which may be often detected by the immune system. Cancer immunotherapy can induce the immune system to attack cancer cells by targeting these antigens. One way to activate anti-tumor immunity is to block immune checkpoint pathways. The immune checkpoint pathway refers to intracellular signaling pathways that maintain self-tolerance and protect tissues from excessive immune response that causes damage. Some immune checkpoints are primary immune evasion mechanisms for tumor cells. Therefore, inhibiting or blocking immune checkpoint may induce activation of T cells, and thus anti-tumor immune may improve.

Transforming growth factor (TGF)-β is a cytokine that regulates cell proliferation and differentiation, wound healing, extracellular matrix production, or the like. TGF-β family belongs to TGF-β superfamily, and this TGF-β superfamily includes activins, inhibins, bone morphogenetic proteins, and anti-Mullerian hormone. The tumor cells and the stromal cells within the tumors in late stages of various cancers generally overexpress TGF-β. TGF-β would lead to stimulation of angiogenesis and cell motility, suppression of the immune system, and increased interaction of tumor cells with the extracellular matrix. TGF-β receptors are serine/threonine kinase receptors, and they are divided into TGF-β receptor 1, TGF-β receptor 2, and TGF-β receptor 3. Of them, TGF-β receptor 1 is also called an activin A receptor type II-like kinase (ALK5).

Accordingly, for effective prevention or treatment of cancer, there is a need for a pharmaceutical composition capable of effectively inhibiting a TGF-β signaling pathway as well as improving antitumor immunity.

DISCLOSURE OF INVENTION

Solution to Problem

Provided is a pharmaceutical composition for preventing or treating cancer, the pharmaceutical composition including a compound having a TGF-β signaling pathway-inhibiting activity and a T lymphocyte activating factor.

Provided is a method of treating or preventing cancer using a compound having a TGF-β signaling pathway-inhibiting activity and a T lymphocyte activating factor.

Advantageous Effects of Invention

A pharmaceutical composition for preventing or treating cancer according to an aspect and a method of preventing or treating cancer using the same may be used to effectively prevent or treat cancer.

BRIEF DESCRIPTION OF DRAWINGS

These and/or other aspects will become apparent and more readily appreciated from the following description of the embodiments, taken in conjunction with the accompanying drawings in which:

FIGS. 1A to 1C are graphs showing the volume of tumor (md) depending on combinations of TEW-7197, anti-CTLA4 antibody, anti-PD-L1 antibody, or anti-PD1 antibody.

MODE FOR THE INVENTION

An aspect provides a pharmaceutical composition for preventing or treating cancer, the pharmaceutical composition including a compound represented by Formula I, a pharmaceutically acceptable salt, solvate, or stereoisomer thereof, or a combination thereof:

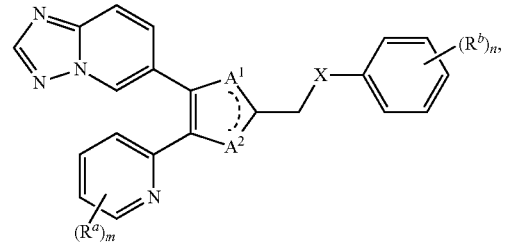

[Formula I]

wherein, in Formula I, $R^a$ may be each independently hydrogen (H), halo, $C_{1-6}$ alkyl, $C_{1-6}$ haloalkyl, $C_{3-6}$ cycloalkyl, OH, —O—$C_{1-6}$ alkyl, —O—$C_{1-6}$ haloalkyl, —O—$C_{3-6}$ cycloalkyl, —$NH_2$, —NH—$C_{1-6}$ alkyl, —NH—$C_{1-6}$ haloalkyl, —NH—$C_{3-6}$ cycloalkyl, —S—$C_{1-6}$ alkyl, —S—$C_{1-6}$ haloalkyl, —S—$C_{3-6}$ cycloalkyl, —CN, or —$NO_2$;

m may be 0, 1, 2, 3, or 4;

any one of $A^1$ and $A^2$ may be N, and the other is $NR^1$, wherein $R^1$ may be H, OH, $C_{1-6}$ alkyl, $C_{1-6}$ haloalkyl, or $C_{3-6}$ cycloalkyl;

X may be a bond, —$(CH_2)_p$—, —$NR^2$—, —O—, or —S—, wherein p may be 0 or 1, and $R^2$ may be H or $C_{1-3}$ alkyl;

$R^b$ may be each independently H, halo, $C_{1-6}$ alkyl, $C_{1-6}$ haloalkyl, $C_{3-6}$ cycloalkyl, $C_{2-6}$ alkenyl, $C_{2-6}$ alkynyl, —$(CH_2)_q$—$OR^3$, —$(CH_2)_q$—$NR^3R^4$, —$(CH_2)_q$—$SR^3$, —$(CH_2)_q$—$NO_2$, —$(CH_2)_q$—CONHOH, —$(CH_2)_q$—CN, —$(CH_2)_q$—$COR^3$, —$(CH_2)_q$—$CO_2R^3$, —$(CH_2)_q$—$CONR^3R^4$, —$(CH_2)_q$-tetrazole, —$(CH_2)_q$—CH=CH—CN, —$(CH_2)_q$—CH=CH—$CO_2R^3$, —$(CH_2)_q$—CH=CH—$CONR^3R^4$, —$(CH_2)_q$—CH=CH-tetrazole, —$(CH_2)_q$—$NHCOR^3$, —$(CH_2)_q$—$NHCO_2R^3$, —$(CH_2)_q$—$CONHSO_2R^3$, —$(CH_2)_q$—$NHSO_2R^3$, —$(CH_2)_q$—C≡C—CN, —$(CH_2)_q$—C≡C—$CO_2R^3$, —$(CH_2)_q$—C≡C—$CONR^3R^4$, —$(CH_2)_q$—C≡C-tetrazole, —$(CH_2)_q$—$SOR^5$, —$(CH_2)_q$—$SO_2R^5$, or —$(CH_2)_r$—$(OR^3)_2$, wherein $R^3$ and $R^4$ may be each independently H, $C_{1-6}$ alkyl, $C_{1-6}$ haloalkyl, or $C_{3-6}$ cycloalkyl, or taken together with a nitrogen atom bound thereto to form a mono-cyclic ring, for example, imidazole, pyrrolidine, piperidine, morpholine, piperazine, and homopiperazine, $R^5$ may be $C_{1-6}$ alkyl, $C_{1-6}$ haloalkyl, or $C_{3-6}$ cycloalkyl, q may be 0, 1, 2, 3, or 4, r may be 1, 2, 3, or 4; and n may be 0, 1, 2, 3, 4, or 5; and a T lymphocyte activating factor.

The alkyl group may be straight or branched. Examples of the alkyl group may include methyl, ethyl, propyl, isopropyl, butyl, isobutyl, sec-butyl, tert-butyl, n-pentyl, and n-hexyl. The alkyl group may be substituted with at least one selected from alkoxy, cycloalkoxy, amino, nitro, carboxy, cyano, halo, hydroxyl, sulfo, mercapto, or a combination thereof.

The cycloalkyl group may be cyclopropyl, cyclobutyl, cyclopentyl, or cyclohexyl.

The halo may be fluorine, chlorine, bromine, or iodine.

The alkenyl group may be straight or branched. The alkenyl group may be vinyl, allyl, isoprenyl, 2-butenyl, or 2-hexenyl. The alkenyl group may be substituted with alkoxy, cycloalkoxy, amino, nitro, carboxy, cyano, halo, hydroxyl, sulfo, mercapto, or a combination thereof.

The alkynyl group may be straight or branched. The alkynyl group may be ethynyl, propargyl, or 2-butynyl. The alkynyl group may be substituted with alkoxy, cycloalkoxy, amino, nitro, carboxy, cyano, halo, hydroxy, sulfo, mercapto, or a combination thereof.

The compound may be a compound represented by Formula II:

[Formula II]

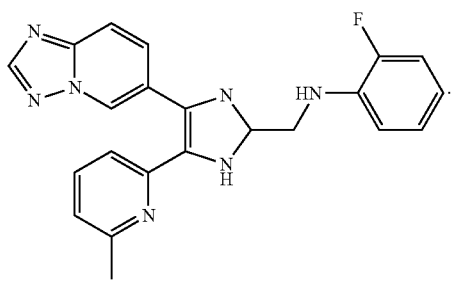

The compound of Formula II may be N-((4-([1,2,4]triazolo[1,5-a]pyridin-6-yl)-5-(6-methylpyridin-2-yl)-1H-imidazol-2-yl)methyl)-2-fluoroaniline.

The compound of Formula I, e.g., the compound of Formula II may selectively inhibit TGF-β receptor 1 (ALK5) and/or activin receptor type-1B (ACVR1B, or ALK4).

The pharmaceutically acceptable salt may be a salt that may not cause significant irritation to an organism to which a compound is administered and may not abrogate the biological activity and properties of the compound. The salt may be, for example, an inorganic acid salt, an organic acid salt, or a metal salt. The inorganic acid salt may be a salt of hydrochloric acid, bromic acid, phosphoric acid, sulfuric acid, or disulfuric acid. The organic acid salt may be a salt of formic acid, acetic acid, propionic acid, lactic acid, oxalic acid, tartaric acid, malic acid, maleic acid, citric acid, fumaric acid, besylic acid, camsylic acid, edisylic acid, trichloroacetic acid, trifluoroacetic acid, benzoic acid, gluconic acid, methanesulfonic acid, glycolic acid, succinic acid, 4-toluenesulfonic acid, galacturonic acid, embonic acid, glutamic acid, ethanesulfonic acid, benzenesulfonic acid, p-toluenesulfonic acid, or aspartic acid. The metal salt may be a calcium salt, a sodium salt, a magnesium salt, a strontium salt, or a potassium salt.

The solvate may be a compound formed by attractive forces between solute and solvent molecules. The solvate may be a hydrate.

The stereoisomer refers to molecules that have the same molecular formula and connectivity of their atoms, but differ in spatial arrangement of atoms. The stereoisomer may be a diastereomer or an enantiomer of the compound of Formula I.

The T lymphocyte activating factor refers to a molecule inducing activation of T cells. The T lymphocyte activating factor may be an immune checkpoint inhibitor, an immune stimulatory molecule, an inhibitor of immunosuppressive factor, or a combination thereof.

The immune checkpoint refers to a molecule in the immune system that either turns up a T cell signal (co-stimulatory molecules) or turns down a T cell signal. The immune checkpoint molecule may be an immune stimulatory molecule or immune inhibitory molecule. The immune stimulatory molecule may be an agonist inducing activation of T cells. The immune stimulatory molecule may be CD27, CD40, OX40, GITR, CD137, CD28, an inducible T cell co-stimulator (ICOS), or a combination thereof.

An inhibition or blockade of the immune checkpoint may refer to inhibition of immunologic tolerance or activation of an immune system. The immune checkpoint blockade may include any of the signaling pathways that activate T cells for the increase of antitumor immune response. The immune checkpoint inhibitor may refer to a molecule that inhibits or blocks the inhibitory checkpoint molecules to activate T cells. The immune checkpoint inhibitor may be an antagonist releasing inhibition of T cells.

The T lymphocyte activating factor may be an agonist that may inhibit signal transduction or reduce expression of a receptor of T cells selected from the group consisting of a programmed cell death protein 1 (PD1), a cytotoxic T-lymphocyte-associated antigen 4 (CTLA4), a B and T lymphocyte attenuator (BTLA), a killer cell immunoglobulin-like receptor (KIR), a lymphocyte activation gene 3 (LAG3), a T cell membrane protein 3 (TIM3), and an adenosine A2a receptor (A2aR). PD1, CTLA4, BTLA, KIR, LAG3, TIM3, and A2aR are receptors of T cells that transmit inhibitory signals of T cells. In this regard, the T lymphocyte activating factor may inhibit signal transduction or reduce expression of PD1, CTLA4, BTLA, KIR, LAG3, TIM3, A2aR, or a combination thereof to activate T cells.

The T lymphocyte activating factor may be an antagonist that may inhibit signal transduction or reduce expression of a surface protein of an antigen-presenting cell (APC) selected from the group consisting of a programmed death-ligand 1 (PD-L1 or PDL1), a programmed death-ligand 2 (PD-L2 or PDL2), a cluster of differentiation (CD) 80, CD86, B7-H3, B7-H4, a herpesvirus entry mediator (HVEM), and galectin 9 (GAL9). PD-L1, PD-L2, CD80, CD86, B7-H3, B7-H4, HVEM, GAL9, or a combination thereof is a surface protein of APC, which may bind to a receptor of T cells that transmits inhibiting signals of T cells. In this regard, the T lymphocyte activating factor may inhibit signal transduction or reduce expression of PD-L1, PD-L2, CD80, CD86, B7-H3, B7-H4, HVEM, GAL9, or a combination thereof to activate T cells.

The T lymphocyte activating factor may be an agonist that activates a receptor of T lymphocytes. The T lymphocyte activating factor may be an agonist that may induce signal transduction or increase expression of a receptor of T lymphocytes selected from the group consisting of CD28, ICOS, CD137, OX40, and CD27. CD28, ICOS, CD137, OX40, and CD27 are receptors of T cells that transmit activation signals of T cells. T cells may be activated by activating signal transduction or increasing expression of the receptor of T lymphocytes. In this regard, the stimulatory checkpoint molecule may activate signal transduction or increase expression of D28, ICOS, CD137, OX40, CD27, or a combination thereof to activate T cells.

The immunosuppressive factor refers to a molecule that inhibits or blocks anti-tumor immune responsiveness. The immunosuppressive factor may a transforming growth factor-β (TGFβ), interleukin (IL)-10, prostaglandin E2 (PGE$_2$), CCL2 (also known as macrophage chemoattractive protein 1: MCP-1), Fas receptor (FasR)/ligand (FasL), cytotoxic T-lymphocyte antigen-4 (CTLA-4), B7-homologue 1 (B7-H1), programmed death ligand-1 (PD-L1), or a combination thereof. The inhibitor of immunosuppressive factor may induce the activity of T cell. The immune-suppressive factor may be one selected from the group consisting of TGFβ, IL-1, IL-6, IL-10, IL-12, and IL18, or an agonist regulating the one selected from the group. The regulating may be suppression or activation of functions, or a decrease or an increase of expression. TGFβ, IL-1, IL-6, IL-10, IL-12, and IL-18 are cytokines, and inhibition of the cytokines may activate T cells.

The agonist, antagonist or inhibitor of immunosuppressive factor may be polypeptide, sugar, nucleic acid, a low molecular weight compound, or a combination thereof. The polypeptide may be an antibody or an antigen-binding fragment thereof. The term "antibody", may be used interchangeably with the term "immunoglobulin (Ig)". A whole antibody has a structure having two full-length light chains and two full-length heavy chains, each light chain binding to the heavy chain via a disulfide bond (SS-bond). The antibody may be IgA, IgD, IgE, IgG, or IgM. The term "antigen-binding fragment" refers to a fragment of a whole structure of Ig, i.e., a portion of polypeptide including a portion to which an antigen may bind. The antigen-binding fragment may be F(ab')2, Fab', Fab, Fv, or scFv. The antibody may be a monoclonal antibody or a polyclonal antibody. Examples of the nucleic acid may include microRNA (miRNA) and small interfering RNA (siRNA).

The T lymphocyte activating factor may be a PD-L1 inhibitor, a PD1 inhibitor, a CTLA4 inhibitor, or a combination thereof. Examples of the PD-L1 inhibitor may include BMS-936559 (MDX1105, Bristol Myers Squibb), MEDI4736 (MedImmune, AstraZeneca), MPDL3280A (Roche), and MSB0010718C (Merck). Examples of the PD1 inhibitor may include AMP-224 (Amplimmune, GlaxoSmith Klein), AMP-514 (MEDI0680, Amplimmune, Glaxo-Smith Klein), nivolumab (Opdivo, Bristol Myers Squibb), Pembrolizumab (Keytruda, Merck), and Pidilizumab (Cure Tech). Examples of the CTLA4 inhibitor may include ipilimumab (Yervoy, Bristol Myers Squibb) and tremelimumab (Pfizer).

The cancer may be solid cancer or non-solid cancer. The solid cancer refers to occurrence of cancerous tumor in organs, e.g. the liver, lung, breast, skin, or the like. The non-solid cancer refers to cancer that occurs in the blood and is also referred to as blood cancer. The cancer may be carcinoma, sarcoma, cancer derived from hematopoietic cells, germ cell tumor, or blastoma. The carcinoma may be cancer derived from epithelial cells. The sarcoma may be cancer derived from connective tissues (i.e., bone, cartilage, fat, and nerves) that may develop from cells derived from mesenchymal cells outside the marrow. The cancer derived from hematopoietic cells may be derived from hematopoietic cells that tend to mature in lymph nodes and blood away from bone marrow. The germ cell tumor may be cancer derived from pluripotent cell. The pluripotent cell may often be present in testes or ovaries. The blastoma may be derived from a immature precursor cell or embryonic tissue. The cancer may be selected from the group consisting of melanoma, cerebrospinal fluid brain tumor, head and neck cancer, lung cancer, breast cancer, thymoma, mesothelioma, esophageal cancer, stomach cancer, colon cancer, liver cancer, pancreatic cancer, biliary tract cancer, kidney cancer, bladder cancer, prostate cancer, testicular cancer, spermocytoma, thyroid cancer, ovarian cancer, cervical cancer, endometrial cancer, lymphoma, myelodysplastic syndromes (MDS), myelofibrosis, acute leukemia, chronic leukemia, multiple myeloma, sarcoma, and skin cancer.

The term "prevention" means all of the actions by which the occurrence of cancer is retarded by the administration of the pharmaceutical composition. The term "treatment" means all of the actions by which the symptoms of cancer have taken a turn for the better or been modified favorably by administration of the pharmaceutical composition.

The pharmaceutical composition may further include a pharmaceutically acceptable carrier. The carrier may mean to include excipients, diluents, or supplements. The carrier may be selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, physiological saline, a buffer, such as PBS, methyl hydroxybenzoate, propyl hydroxybenzoate, talc, magnesium stearate, mineral oil, and the like. The composition may include a filler, an anti-coagulating agent, a lubricant, a humectant, a flavor, an emulsifier, an antiseptic, or the like.

The pharmaceutical composition may be prepared in any formulation based on conventional methods. The composition may be formulated in an oral dosage form (e.g., powder, tablet, capsule, syrup, pill, or granule) or a parenteral dosage form (e.g., injectable formulation). In addition, the composition may be prepared in systemic dosage forms or topical dosage forms.

The pharmaceutical composition may be a single composition or individual compositions. For example, the pharmaceutical composition of the compound of Formula I, a pharmaceutically acceptable salt, solvate, stereoisomer thereof, or a combination thereof may be a composition in an oral dosage form, and T lymphocyte activating factor may be a composition in an abdominal dosage form.

The pharmaceutical composition may include the compound of Formula I, a pharmaceutically acceptable salt, solvate, stereoisomer thereof, or a combination thereof; and the T lymphocyte activating factor in an effective amount. The term "effective amount" means a sufficient amount to show prevention or treatment effect when administered to a subject in need of prevention or treatment. The effective amount may appropriately selected by one of ordinary skill in the art depending on the selected cell or subject. The effective amount may be determined according to factors including the severity of a disease, patient's age, weight, health conditions, sex, sensitivity to drug, drug administration time, administration route, discharge rate, treatment period, and drugs which are mixed or used in combination with the composition, and other factors which are well known in the medical field. The effective amount may be in a range of about 0.5 µg to about 2 g, about 1 µg to about 1 g, about 10 μg to about 500 mg, about 100 μg to about 100 mg, or about 1 mg to about 50 mg based on the pharmaceutical composition.

An administration dose of the pharmaceutical composition may be, for example, in a range of about 0.001 mg/kg to about 100 mg/kg, about 0.01 mg/kg to about 10 mg/kg, or about 0.1 mg/kg to about 1 mg/kg for adults, once a day, several times a day, once to four times a month, or once to twelve times a year.

Another aspect provides a method of preventing or treating cancer, the method including administering the compound of Formula I according to an aspect, a pharmaceutically acceptable salt, solvate, or stereoisomer thereof, or a combination thereof and a T lymphocyte activating factor to a subject.

The compound of Formula I, a pharmaceutically acceptable salt, solvate, or stereoisomer thereof, the T lymphocyte activating factor, cancer, prevention, and treatment are the same as described above.

The subject may be humans, cattle, horses, pigs, dogs, sheep, goats, or cats. The subject may be a subject having cancer or high possibility of having cancer.

The administration of the compound, a pharmaceutically acceptable salt, solvate, stereoisomer thereof, or a combination thereof, and the T lymphocyte activating factor may be performed directly by any suitable method, e.g., oral, intravenous, intramuscular, transdermal, mucosal, intranasal, intratracheal, or subcutaneous administration. The compound, a pharmaceutically acceptable salt, solvate, stereoisomer thereof, or a combination thereof, and the T lymphocyte activating factor may be systemically or topically administered singly or together with another pharmaceutically active compound.

The compound, a pharmaceutically acceptable salt, solvate, stereoisomer thereof, or a combination thereof, and the T lymphocyte activating factor may be administered simultaneously, individually, or sequentially.

A preferred administration dose of the compound, a pharmaceutically acceptable salt, solvate, stereoisomer thereof, or a combination thereof, and the T lymphocyte activating factor may differ depending on a patient's conditions and body weight, severity of the disease, drug formulation, administration route and period, but it may be properly selected by one of ordinary skill in the art. The administration dose may be, for example, in a range of about 0.001 mg/kg to about 100 mg/kg, about 0.01 mg/kg to about 10 mg/kg, or about 0.1 mg/kg to about 1 mg/kg for adults, once a day, several times a day, once to four times a month, or once to twelve times a year.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items.

Hereinafter, the present invention will be described in more detail with reference to Examples. However, these Examples are for illustrative purposes only, and the invention is not intended to be limited by these Examples.

Example 1. Test of Anti-Tumor Effects in Mouse Model Xenotransplanted with Melanoma Cell 1. Preparation of Mouse Model and Drug In order to validate in vivo anti-tumor effects, female 5 week-old SPF C57BL/6 mice were purchased from Koatech Co. (South Korea). These mice were maintained in a room controlled at a temperature of about 22° C. while freely supplying food and water to them. 1 week after, $5 \times 10^4$ cells of B16F10 melanoma cell line (ATCC, CRL-6475™) were injected to these 6 week-old mice by subcutaneous injection. 8 week-old mice, 2 weeks after the injection of melanoma cell line, were used in the experiment.

As a carrier, 7 ml of 37% (v/v) gastric acid, 2.0 g of NaCl, 3.2 g of pepsin (Sigma-Aldrich), and distilled water were mixed together to prepare 1,000 ml of artificial gastric fluid. As an administration drug, N-((4-([1,2,4]triazolo[1,5-a]pyridin-6-yl)-5-(6-methylpyridin-2-yl)-1H-imidazol-2-yl)methyl)-2-fluoroaniline (hereinafter, referred to as "TEW-7197") (Syngene, India) was dissolved in the carrier to prepare 2.5 mg/ml of TEW-7197 solution.

As for another administration drug, anti-PD-L1 monoclonal antibody (prepared by requesting to ANR therapeutics co., Ltd., host cell: HEK293F), anti-PD1 monoclonal hamster antibody (BioXCell, Cat. No. BE0033-2), anti-CTLA4 monoclonal hamster antibody (BioXCell, Cat. No. BE0131), human immunoglobulin G (IgG) (Thermo Scientific, Cat. No. 31154), and monoclonal hamster IgG (BioXCell, Cat. No. BE0091) were prepared.

2. Drug Administration to Mouse Model and Measurement of Weight Caused by Administration Drug The mouse models prepared in 1. were orally administered with 2.5 mg/ml of a TEW-7197 solution at a dose of 25 mg/weight kg once a day for 5 consecutive days of a week. Then, during the last 2 days, the TEW-7197 solution was not administered to them. These mice were administered with antibody at a dose of about 100 μg per mouse once every 2 days by abdominal injection. As for a control group for TEW-7197, a carrier administered group was used. As for a control group for antibody, a human IgG administered group and a hamster IgG administered group were used.

The drugs administered to the mouse models are shown in Table 1.

TABLE 1

| Group (6 mice/group) | Administration drug |
|---|---|
| 1 | Vehicle |
| 2 | Human IgG |
| 3 | Hamster IgG |
| 4 | Anti-PD-L1 antibody |
| 5 | Anti-PD1 antibody |
| 6 | Anti-CTLA4 antibody |
| 7 | Anti-PD-L1 antibody + TEW-7197 |
| 8 | Anti-PD1 antibody + TEW-7197 |
| 9 | Anti-CTLA4 antibody + TEW-7197 |
| 10 | TEW-7197 |

From the day that the drugs were administered (start date) to the 11th day, the weights of mice were measured every 2 days. The changes in mice (%) (average (%)±standard deviation) caused by drug administration are shown in Table 2.

TABLE 2

| Group | Administration drug | Start date | \multicolumn{5}{c}{Days after administration} |
| | | | 2 | 4 | 6 | 8 | 11 |
|---|---|---|---|---|---|---|---|
| 1 | Vehicle | 100.0 ± 0.0 | 105.5 ± 1.3 | 108.6 ± 0.6 | 111.5 ± 0.7 | 117.3 ± 1.5 | 127.2 ± 4.6 |
| 2 | Human IgG | 100.0 ± 0.0 | 106.0 ± 0.9 | 110.5 ± 2.3 | 112.9 ± 2.6 | 119.3 ± 3.2 | 129.9 ± 5.2 |
| 3 | Hamster IgG | 100.0 ± 0.0 | 104.3 ± 0.7 | 107.7 ± 1.1 | 109.4 ± 1.9 | 118.5 ± 1.4 | 128.3 ± 3.1 |
| 4 | Anti-PD-L1 antibody | 100.0 ± 0.0 | 104.2 ± 2.1 | 107.0 ± 3.7 | 108.9 ± 4.1 | 115.0 ± 5.6 | 125.3 ± 4.9 |
| 5 | Anti-PD1 antibody | 100.0 ± 0.0 | 103.9 ± 2.5 | 107.1 ± 2.8 | 109.1 ± 4.1 | 117.1 ± 1.9 | 126.8 ± 1.8 |
| 6 | Anti-CTLA4 antibody | 100.0 ± 0.0 | 103.8 ± 1.2 | 106.8 ± 1.7 | 108.9 ± 1.5 | 116.6 ± 2.2 | 126.4 ± 4.9 |
| 7 | Anti-PD-L1 antibody + TEW-7197 | 100.0 ± 0.0 | 104.0 ± 1.0** | 106.5 ± 3.9 | 108.5 ± 4.3 | 114.7 ± 4.0 | 123.9 ± 4.6 |
| 8 | Anti-PD1 antibody + TEW-7197 | 100.0 ± 0.0 | 103.8 ± 2.5 | 106.9 ± 3.2 | 108.7 ± 3.0 | 116.0 ± 4.0 | 125.2 ± 3.3 |
| 9 | Anti-CTLA4 antibody + TEW-7197 | 100.0 ± 0.0 | 103.7 ± 3.3 | 106.2 ± 1.3 | 108.2 ± 2.2 | 116.0 ± 2.9 | 125.2 ± 2.7 |
| 10 | TEW-7197 | 100.0 ± 0.0 | 104.3 ± 1.2 | 106.7 ± 3.5 | 108.7 ± 4.5 | 115.8 ± 6.4 | 125.0 ± 6.5 | t-TEST: **p < 0.01 (vs. human IgG administered group)

As shown in Table 2, mice barely had significant weight change caused by anti-PD-L1 antibody, anti-PD1 antibody, anti-CTLA4 antibody, TEW-7197, and a combination thereof.

3. Test of Tumor Inhibitory Effects of Drug in Mouse Model

As described in 2., drug administration was carried out, and then 20 minutes after the last dose of the drug, mice were sacrificed, tumors were resected from the mice. Tumor volume was measured with calipers and calculated using Equation 1:

$$\text{Tumor volume (mm}^3) = [\text{length (mm)} \times \text{width (mm)} \times \text{height (mm)}]/2 \quad [\text{Equation 1}]$$

The difference between the initial tumor volume ($V_0$) in the start date and the tumor volume after drug administration ($V_t$) was calculated, to calculate the change in tumor volume ($\Delta t = V_t - V_0$). From the calculated tumor volume, the tumor inhibition rate (%) by drug administration was calculated. The results thereof are shown in Table 3.

TABLE 3

| Group | Administration drug | | Start date | 2 | 4 | 6 | 8 | 11 |
|---|---|---|---|---|---|---|---|---|
| 1 | Vehicle | Tumor volume change† | 0.0 ± 0.0 | 38.6 ± 6.3 | 128.2 ± 18.9 | 226.7 ± 16.1 | 590.3 ± 85.9 | 1371.0 ± 139.3 |
| 2 | Human IgG | Tumor volume change† | 0.0 ± 0.0 | 40.3 ± 6.5 | 135.5 ± 22.4 | 239.4 ± 25.6 | 610.4 ± 67.8 | 1566.9 ± 109.2 |
| 3 | Hamster IgG | Tumor volume change† | 0.0 ± 0.0 | 46.5 ± 6.9 | 139.5 ± 20.0 | 243.0 ± 18.5 | 600.3 ± 72.3 | 1468.5 ± 154.9 |
| 4 | Anti-PD-L1 antibody | Tumor volume change† | 0.0 ± 0.0 | 34.5 ± 5.8 | 115.2 ± 13.2 | 197.6 ± 30.5* | 497.4 ± 60.1* | 1313.9 ± 112.7** |
| | | Inhibition rate‡ | | 14.4% | 15.0% | 17.5% | 18.5% | 16.1% |
| 5 | Anti-PD1 antibody | Tumor volume change† | 0.0 ± 0.0 | 41.2 ± 5.8 | 125.1 ± 8.3 | 215.7 ± 27.8 | 536.7 ± 73.0 | 1354.0 ± 122.3 |
| | | Inhibition rate‡ | | 11.3% | 10.3% | 11.2% | 10.6% | 7.8% |
| 6 | Anti-CTLA4 antibody | Tumor volume change† | 0.0 ± 0.0 | 40.0 ± 5.6 | 117.5 ± 11.8* | 206.9 ± 23.5* | 533.3 ± 80.5 | 1338.3 ± 127.2 |
| | | Inhibition rate‡ | | 14.1% | 15.8% | 14.8% | 11.1% | 8.9% |
| 7 | Anti-PD-L1 antibody + TEW-7197 | Tumor volume change† | 0.0 ± 0.0 | 29.2 ± 2.8** | 98.5 ± 11.8** | 156.3 ± 33.0*** | 365.3 ± 78.5*** | 934.7 ± 130.3*** |
| | | Inhibition rate‡ | | 27.5% | 27.3% | 34.7% | 40.2% | 40.3% |

TABLE 3-continued

| Group | Administration drug | | Start date | Days after administration | | | | |
|---|---|---|---|---|---|---|---|---|
| | | | | 2 | 4 | 6 | 8 | 11 |
| 8 | Anti-PD1 antibody + TEW-7197 | Tumor volume change† | 0.0 ± 0.0 | 36.7 ± 6.6* | 107.8 ± 19.6* | 175.4 ± 31.0*** | 436.6 ± 61.9** | 1066.2 ± 194.0** |
| | | Inhibition rate‡ | | 21.0% | 22.7% | 27.8% | 27.3% | 27.4% |
| 9 | Anti-CTLA4 antibody + TEW-7197 | Tumor volume change† | 0.0 ± 0.0 | 34.3 ± 3.7** | 100.1 ± 13.7** | 172.4 ± 30.5*** | 420.7 ± 53.7*** | 1048.2 ± 167.9** |
| | | Inhibition rate‡ | | 26.3% | 28.2% | 29.0% | 29.9% | 28.6% |
| 10 | TEW-7197 | Tumor volume change† | 0.0 ± 0.0 | 30.4 ± 6.6 | 100.4 ± 11.4* | 174.5 ± 29.6** | 455.3 ± 67.1* | 1084.0 ± 179.5* |
| | | Inhibition rate‡ | | 21.3% | 21.7% | 23.0% | 22.9% | 20.9% | t-TEST:
*$p < 0.05$,
**$p < 0.01$,
***$p < 0.001$ (vs. vehicle administered group, human IgG administered group, or hamster IgG administered group),
†$\Delta t = V_t - V_0$, and
‡tumor inhibition rate (%) (vs. vehicle administered group, human IgG administered group, or hamster IgG administered group)

As shown in Table 3, at the 11th day, the tumor inhibition rate of the anti-PD-L1 antibody and TEW-7197 administered group (Group 7) was about 2.5 times higher than that of the anti-PD-L1 antibody administered group (Group 4) and about 1.9 times higher than that of the TEW-7197 administered group (Group 10). At the 11th day, the tumor inhibition rate of the anti-PD1 antibody and TEW-7197 administered group (Group 8) was about 3.5 times higher than that of the anti-PD1 antibody administered group (Group 5) and about 1.3 times higher than that of the TEW-7197 administered group (Group 10). At the 11th day, the tumor inhibition rate of the anti-CTLA4 antibody and TEW-7197 administered group (Group 9) was about 3.2 times higher than that of the anti-CTLA4 antibody administered group (Group 6) and about 1.3 times higher than that of the TEW-7197 administered group (Group 10).

Accordingly, the combination of anti-PD-L1 antibody, anti-PD1 antibody, and anti-CTLA4 antibody as immune checkpoint inhibitors and TEW-7197 as an inhibitor of TGF-β receptor was found to have significant tumor inhibitory effect, as compared with each of the anti-PD-L1 antibody, anti-PD1 antibody, anti-CTLA4 antibody, and TEW-7197.

4. Test of Synergistic Combination of Drugs in Mouse Model

Test of tumor inhibitory effect by synergistic combination of immune checkpoint inhibitors and inhibitor of TGF-β receptor was carried out.

In detail, as described in 1., C57BL/6 mice were prepared, and 1×10⁴ cells of B16F10 melanoma cell line (ATCC, CRL-6475™) were injected to each of the mice. When the average tumor size of each group reached about 26.0 mm³, drug administration was carried out.

As described in 1., TEW-7197, anti-CTLA4 antibody, anti-PD-L1 antibody, anti-PD1 antibody, human IgG, and hamster IgG were prepared as drugs.

The prepared mice were orally administered with a TEW-7197 solution at a dose of 10 mg/weight kg once a day for 5 consecutive days of a week. Then, during the last 2 days, the TEW-7197 solution was not administered. These mice were administered with antibody at a dose of about 100 μg per mouse once every 2 days by abdominal injection. In a negative control group, a vehicle was administered for TEW-7197, and human IgG or hamster IgG was administered for antibody. 11 days after the drug administration, tumor volume was measured with calipers and calculated as described in 3.

The tumor volume according to combinations of TEW-7197 and anti-CTLA4 antibody, anti-PD-L1 antibody, or anti-PD1 antibody are shown in FIGS. 1A to 1C.

As shown in FIG. 1A, the tumor volume of the anti-CTLA4 antibody administered group, the TEW-7197 administered group, and the combination of anti-CTLA4 antibody and TEW-7197 administered group was decreased by about 14.5%, about 10.1%, and about 27.1, as compared with the tumor volume of the negative control group, respectively.

As shown in FIG. 1B, the tumor volume of the anti-PD-L1 antibody administered group, the TEW-7197 administered group, and the combination of anti-PD-L1 antibody and TEW-7197 administered group was decreased by about 15.0%, about 9.2%, and about 28.8%, as compared with the tumor volume of the negative control group, respectively.

As shown in FIG. 1C, the tumor volume of the anti-PD1 antibody administered group, the TEW-7197 administered group, and the combination of anti-PD1 antibody and TEW-7197 administered group was decreased by about 9.6%, about 8.1%, and about 23.3%, as compared with the tumor volume of the negative control group, respectively.

Accordingly, the combination of anti-PD-L1 antibody, anti-PD1 antibody, and anti-CTLA4 antibody as immune checkpoint inhibitors and TEW-7197 as an inhibitor of TGF-β receptor was found to have synergistic tumor inhibitory effect, as compared with each of the anti-PD-L1 antibody, anti-PD1 antibody, anti-CTLA4 antibody, and TEW-7197.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the inventive concept as defined by the following claims.

The invention claimed is:

1. A method of treating melanoma comprising:
   administering a compound represented by Formula II, a pharmaceutically acceptable salt, solvate, or stereoisomer thereof, and a T lymphocyte activating factor to a subject:

[Formula II]

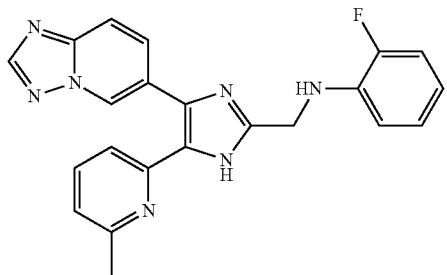

wherein the T lymphocyte activating factor is an anti-programmed cell death protein 1 (PD1) antibody, an anti-cytotoxic T-lymphocyte-associated antigen 4 (CTLA4) antibody, or an anti-programmed death ligand 1 (PD-L1) antibody.

2. The method of claim 1, wherein the anti-programmed cell death protein 1 (PD1) antibody inhibits signal transduction or reduces expression of PD1.

3. The method of claim 1, wherein the anti-cytotoxic T-lymphocyte-associated antigen 4 (CTLA4) antibody inhibits signal transduction or reduces expression of CTLA4.

4. The method of claim 1, wherein the anti-programmed death ligand 1 (PD-L1) antibody inhibits signal transduction or reduces expression of PD-L1.

5. The method of claim 1, wherein the T lymphocyte activating factor is an anti-programmed death ligand 1 (PD-L1) antibody.

6. The method of claim 1, wherein the T lymphocyte activating factor is an anti-programmed cell death protein 1 (PD1) antibody.

7. The method of claim 1, wherein the T lymphocyte activating factor is an anti-cytotoxic T-lymphocyte-associated antigen 4 (CTLA4) antibody.

8. The method of claim 1, wherein the administering is performed simultaneously, individually, or sequentially.

* * * * *